United States Patent [19]

Jones et al.

[11] 4,289,767
[45] Sep. 15, 1981

[54] 5-(CHLOROPHENYL)-6H-1,3,4-THIADIAZINE-2-AMINES

[75] Inventors: Winton D. Jones, Cincinnati; Francis P. Miller, Loveland, both of Ohio

[73] Assignee: Richardson-Merrell Inc., Wilton, Conn.

[21] Appl. No.: 71,952

[22] Filed: Sep. 4, 1979

[51] Int. Cl.³ .................... C07D 285/16; A61K 31/54
[52] U.S. Cl. ........................................ 424/246; 544/8
[58] Field of Search ............................ 424/246; 544/8

[56] References Cited

U.S. PATENT DOCUMENTS

| | | | |
|---|---|---|---|
| 2,871,237 | 1/1959 | Gregory | 260/243 |
| 3,428,631 | 2/1969 | Trepanier et al. | 260/243 |
| 3,862,183 | 1/1975 | Doyle | 544/8 |
| 4,158,732 | 6/1979 | Cleveland et al. | 544/8 |

FOREIGN PATENT DOCUMENTS 49-88889 8/1974 Japan.

OTHER PUBLICATIONS

Ishizuka, *Chemical Abstracts*, vol. 82, entry 59824t, (1975).
Yoshida et al., *Chemical Abstracts*, vol. 82, entry 57744t, 171096h, 171095g, 170912j, (1975).
Derwent Abstract 80095v/46 for Japanese Pat. No. 74-88889.
Robbins et al., *Proc. Natl. Acad. Sci.*, vol. 24, pp. 141-145, (1938).
Ban, *J. Pharm. Soc., Japan*, vol. 73, pp. 533-537, (1953).
Bilinski et al., *Chemical Abstracts*, vol. 63, entry 10863h, (1965).
Trepanier et al., *J. Med. Chem.*, vol. 10(6), pp. 1085-1087, (1967).
Rao, Khim; Geterotsiki, Soedin; 1977 (3), pp. 291-310.
Klosa, *Arch. Pharm.*, vol. 287, pp. 12-14, (1954).
Beyer et al., *Justus Liebigs Ann. Chem.*, vol. 741, pp. 45-54, (1970).
Pfeiffer et al., *Z. Chem.*, 17(6), pp. 218-220, (1977).

*Primary Examiner*—John M. Ford
*Attorney, Agent, or Firm*—John J. Kolano; Raymond A. McDonald; William J. Stein

[57] ABSTRACT

Compounds of the formula

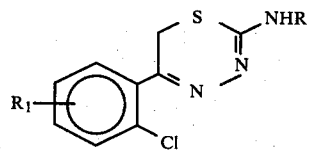

wherein R is H, $C_{1-5}$ or 7-straight or branched chain alkyl or allyl and $R_1$ is H or Cl and the pharmacologically acceptable acid addition salts thereof are pharmacologically active as anticonvulsant and anxiolytic agents.

9 Claims, No Drawings

5-(CHLOROPHENYL)-6H-1,3,4-THIADIAZINE-2-AMINES

RELATIONSHIP TO OTHER APPLICATIONS

This application is related to copending application Ser. Nos. 071,954, 071,970, 072,793 and 071,966, all filed Sept. 4, 1979.

BACKGROUND OF THE INVENTION

The present invention relates to 5-(chlorophenyl)-6H-1,3,4-thiadiazine-2-amines, having anticonvulsant and anxiolytic activity.

As a general class, 5-(optionally substituted phenyl)-6H-1,3,-4-thiadiazine-2-amines are known as chemical intermediates. See, for example, Japanese Patents 74-110,696, 74-110,697 and 74-100,080. Many individual species related to the compounds of this invention are also known as chemical intermediates. See, for example:

1. Japanese Patent 75 37651;
2. McLean et al, J. Chem. Soc. 1937, 556–9;
3. Avramovici, Analele stiint. univ. "Al. I. Cuza" Iasi, Sect. 1 (Mat. Fiz., chim.). (N.S.) 1, 315–319 (1955). CA51:10541;
4. Beyer et al, Justus Liebigs Ann. Chem. 741, 45–54 (1970);
5. Japanese Pat. No. 74-110,696;
6. Japanese Pat. No. 74-110,697;
7. Bose, Quart. J. Indian Chem. Soc. 1, 51–62 (1924).
8. Beyer et al, Chem. Ber. 89, 107–14 (1956);
9. Japanese Pat. No. 74-88,889;
10. Japanese Pat. No. 74-100,080;
11. Bose, Quart. J. Ind. Chem. Soc. 2, 95–114 (1925).
12. Bose et al, J. Indian Chem. Soc. 7, 733–9 (1930);
13. Bulka et al, Z. Chem. 15(12), 482 (1965);
14. Schmidt et al, Tetrahedron Lett. 1975 (1), 33–6;
15. Beyer, Quart. Rep. Sulfur Chem. 5(3), 177–89 (1970);
16. Saraswathi et al, Indian J. Chem. 10(12), 1151–4 (1972);
17. Hampel, Z. Cham. 9(2), 61–2 (1969);
18. Pfeiffer et al, Z. Chem. 17(6), 218–20 (1977);
19. Pfeiffer et al, Synthesis 1977(7), 485–6; and
20. Pfeiffer et al, Synthesis 1977(3), 196–8. Certain species are further known as flame retardants (Japanese Pat. No. 74-5439).

Moreover, some 2-amino-1,3,4-thiadiazines are generally known to have antiviral, antiinflammatory and analgesic activity (Japanese Pat. No. 74-88889). Additionally, many individual species related in structure to the compounds of this invention are disclosed in this same reference. Some species have been found ineffective as vitamin B substitutes (Robbins et al, Proc. Natl. Acad. Sci. U.S. 24, 141–5 (1938) and antitubercular agents (Ban., J. Pharm. Soc. Japan 73, 533–7 (1953) and Bilinski et al, Bull. Acad. Polon. Sci., Ser. Sci. Chim. 13(6), 393–6 (1965)).

Other compounds having significantly different structures are also known to possess pharmacological activity.

4-methyl-4H-5,6-dihydro-1,3,4-thiadiazin-2-amines are known to be CNS active (U.S. Pat. No. 3,428,631 and Trepanier et al, J. Med. Chem. 10(6), 1085–7 (1967)). Additionally, 3-substituted-1,2-dihydro-1,3,4-thiadiazin-2-imines are known as slow cure accelerators for rubber (U.S. Pat. No. 2,871,237).

The 5-membered ring-containing 2-amino-1,3,4-thiadiazoles are known to possess CNS depressant activity (Maffii et al, Il Farmaco (Pavia) Ed. Sci. 13, 187–217 (1958); Great Britain Pat. No. 815,188; W. German Pat. No. 2,212,245 (or Great Britain Pat. No. 1,380,136); U.S. Pat. No. 3,965,110; U.S. Pat. No. 4,054,665; U.S. Pat. No. 3,919,428; and U.S. Pat. No. 3,992,396) and antihypertensive activity (U.S. Pat. No. 3,746,716).

These 5-membered ring-containing 1,3,4-thiadiazole-2-amines are a class of compounds treated by the prior art as distinct from the 6-membered ring-containing 1,3,4-thiadiazin-2-amines. However, the preparation of both types of compounds are reported together by Rao, Khim. Geterotsikl. Soedin. 1977(3), 291–310, as does Klosa, Arch. Pharm. 287, 12–14 (1954). In the latter reference, the compounds are reported as potential, but untested, tuberculostatics. Compounds of both types are also disclosed in Japanese Pat. No. 74 5439 as fire retardants.

SUMMARY OF THE INVENTION

Compounds of Formula I

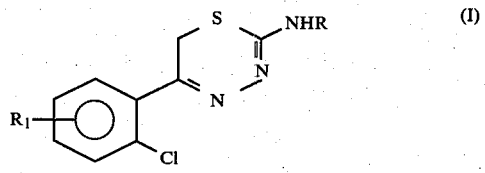

wherein R is H, $C_{1-5 \text{ or } 7}$-straight or branched chain alkyl or allyl and $R_1$ is H or Cl, and the pharmaceutically acceptable acid addition salts thereof, are useful as anticonvulsant and anxiolytic agents.

DETAILED DESCRIPTION OF THE INVENTION

Illustrative examples of straight or branched chain $C_{1-5}$ alkyl groups mentioned above in all instances in describing the group R include, for example, methyl, ethyl, n-propyl, isopropyl, n-butyl, sec-butyl, isobutyl, tert-butyl, n-pentyl, isopentyl, neopentyl, etc. Illustrative examples of straight or branched chain $C_7$ alkyl groups which R may represent as used herein include, for example, n-heptyl, isoheptyl, etc.

Pharmaceutically acceptable acid addition salts of the compounds of Formula I include those of any suitable inorganic or organic acid. Suitable inorganic acids are, for example, hydrochloric, hydrobromic, sulfuric or phosphoric acid. Suitable organic acids are, for example, carboxylic acids, such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicyclic and 2-phenoxybenzoic, or sulfonic acids such as, for example, methanesulfonic and 2-hydroxyethane-sulfonic acid.

Of the compounds of Formula I, those wherein $R_1$ is Cl, preferably 4-Cl, especially those wherein also R is $C_{1-5}$ straight or branched chain alkyl or allyl, are preferred. Thus, preferred compounds include 5-(2,4-dichlorophenyl)-N-methyl-6H-1,3,4-thiadiazin-2-amine, 5-(2,4-dichlorophenyl)-N-ethyl-6H-1,3,4-thiadiazin-2-amine, 5-(2,4-dichlorophenyl)-N-propyl-6H-1,3,4-thiadiazin-2-amine, N-butyl-5-(2,4-dichlorophenyl)-6H-1,3,4-thiadiazin-2-amine and 5-(2,4-dichlorophenyl)-N-pentyl-6H-1,3,4-thiadiazin-2-amine, 5-(2,4-D-dichlorophenyl)-N-2-propenyl-6H-1,3,4-thiadiazin-2-amine and their acid addition salts.

Illustrative examples of compounds of this invention include, for example, 5-(2,4-dichlorophenyl)-N-pentyl-6H-1,3,4-thiadiazin-2-amine, N-butyl-5-(2,4-dichlorophenyl)-6H-1,3,4-thiadiazin-2-amine, 5-(2,4-dichlorophenyl)-N-propyl-6H-1,3,4-thiadiazin-2-amine, 5-(2,5-dichlorophenyl)-N-methyl-6H-1,3,4-thiadiazin-2-amine, 5-(2,4-dichlorophenyl)-N-ethyl-6H-1,3,4-thiadiazin-2-amine, 5-(2-chlorophenyl)-N-methyl-6H-1,3,4-thiadiazin-2-amine, 5-(2,4-dichlorophenyl)-N-methyl-6H-1,3,4-thiadiazin-2-amine and 5-(2,4-dichlorophenyl)-6H-1,3,4-thiadiazin-2-amine, 5-(2,4-dichlorophenyl)-N-2-propenyl-6H-1,3,4-thiadiazin-2-amine, 5-(2,4-dichlorophenyl)-N-heptyl-6H-1,3,4-thiadiazin-2-amine and the acid addition salts of each.

The compounds of this invention are useful as anticonvulsant and anxiolytic agents and, thus, as tranquilizers. These compounds can be administered to warm-blooded animals, mammals, rats, mice, dogs, cats, horses, pigs, cows, sheep, and humans. As used herein, the term "patient" is intended to mean the animal or mammal being treated.

The pharmacological activities of the compounds of the compounds of this invention may be illustrated by their effectiveness in standard pharmacological screening tests. For example, their anticonvulsant and anxiolytic efficacy may be demonstrated by their inhibition of clonic seizures induced by injection of metrazole in mice (Metrazole Antagonism Test).

Especially advantageous aspects of the compounds of this invention include a favorable spectrum of activity, low addiction liability and abuse potential, and a favorable dissociation between desired activity and unwanted side effects such as induction of sedation.

The compounds of this invention can be administered orally or parenterally either alone or in the form of a pharmaceutical preparation. Pharmaceutical preparations containing conventional pharmaceutical carriers and as active ingredients compounds of this invention can be employed in unit dosage forms such as solids, for example, tablets, capsules, and pills, or liquid solutions, suspensions, or emulsions for oral and parenteral administration. The dosage unit administered can be any anticonvulsant or anxiolytic effective amount. The quantity of compound administered can vary over a wide range to provide from about 30 to about 50 mg/kg of body weight of the patient per day, to achieve the desired effect. Unit doses can contain about 5–500 mg of a compound of Formula I and may be administered, for example, from 1 to 4 times daily.

The compounds of Formula I are prepared by reacting a phenacyl halide of the formula

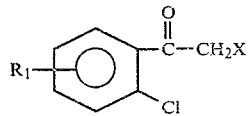

with a 4-substituted thiosemicarbazide of the formula

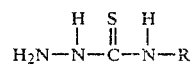

wherein X is Cl or Br and R, and $R_1$ are as hereinbefore defined. The reaction is generally conducted in the presence of a solvent, e.g., a lower alkanol, such as, methanol, ethanol, isopropanol, n-propanol, n-butanol and the like, preferably methanol. The reaction time may vary from about 15 minutes to about 1 hour, preferably about 30 minutes, depending upon the reactants, the solvent and the reaction temperature which may vary from about 60° C. to about 80° C., preferably around 65° C. The product is generally worked-up by permitting the reaction mixture to cool and then concentrating it in vacuo. The resultant residue is recrystalized from an appropriate solvent, e.g., a mixture of a lower alkanol with, e.g., acetone, butanone or ethyl acetate, e.g., methanol/acetone or methanol/ethyl acetate, producing the compound of Formula I as its hyrohalide salt.

Both the phenacyl halide and the 4-substituted thiosemicarbazide which are employed as starting materials in the preparation of the compounds of Formula I are either commercially available or, when unavailable, are very readily preparable by standard chemical reactions which are well-known to those of ordinary skill in the art. For example, the phenacyl halides may be prepared by halogenating the corresponding methyl chlorophenyl ketone using a sulfuryl halide, e.g., sulfuryl chloride, in, e.g., acetic acid, e.g., to prepare the corresponding phenacyl chloride; or by reacting the corresponding chlorobenzene with a haloacetyl halide, e.g., chloroacetyl chloride via a Friedel Crafts reaction using an aluminum trichloride catalyst, e.g., to prepare the corresponding phenacyl chloride. The 4-substituted thiosemicarbazides may be prepared by conventionally reacting the appropriate substituted isothiocyanate with hydrazine in the presence, e.g., of diethyl ether.

EXAMPLES

The following examples are illustrative of the invention.

EXAMPLE 1

5-(2,4-Dichlorophenyl)-N-pentyl-6H-1,3,4-thiadiazin-2-amine monohydrochloride 4.84 g (0.03 mole) of 4-N-pentyl-thiosemicarbazide and 6.70 g (0.03 mole) of (2,4-dichlorophen)acyl chloride are heated and stirred at reflux (65° C.) in 175 ml of methanol for 30 minutes. At this time, the solvent is removed in vacuo. The residue is dissolved in methanol, warmed and then diluted with acetone. Subsequently, it is concentrated to a volume of approximately 200 ml. 6.7 g of 5-(2,4-dichlorophenyl)-N-pentyl-6H-1,3,4-thiadiazin-2-amine monohydrochloride precipitate out as a white solid. m.p. 171°–173° C. The solid is subsequently dried under high vacuum at 78° C.

EXAMPLE 2

N-Butyl-5-(2,4-dichlorophenyl)-6H-1,3,4-thiadiazin-2-amine monohydrochloride

Utilizing the procedures of EXAMPLE 1, 4.47 g (0.014 mole) of (2,4-dichlorophen)acyl chloride and 2.66 g (0.014 mole) of 4-N-butylthiosemicarbazide are reacted, except that 150 ml of methanol are used as the solvent. The resultant precipitate is recrystallized from methanol/ethyl acetate yielding 3.98 g of a white solid, N-butyl-5-(2,4-dichlorophenyl)-6H-1,3,4-thiadiazin-2-amine monohydrochloride, m.p. 180°–182° C. The solid is subsequently dried at 78° C. under high vacuum.

EXAMPLES 3–7

Utilizing the conditions of EXAMPLE 2, the following compounds (starting from the mentioned reactants) were prepared: p EXAMPLE 3-5-(2,4-dichlorophenyl)-N-propyl-6H-1,3,4-thiadiazin-2-amine monohydrochloride (6.4 g) (from (2,4-dichlorophen)acyl chloride (6.70 g-0.03 mole) and 4-n-propyl-thiosemicarbazide (3.99 g-0.03 mole)). m.p. 184°–185° C.;

EXAMPLE 4-5-(2,5-dichlorophenyl)-N-methyl-6H-1,3,4-thiadiazin-2-amine monohydrochloride (from (2,5-dichlorophen)acyl chloride (5.58 g) and 4-methyl-thiosemicarbazide (2.63 g)). m.p. 193°–194.5° C.

EXAMPLE 5-5-(2,4-dichlorophenyl)-N-ethyl-6H-1,3,4-thiadiazin-2-amine monohydrochloride (6.5 g) (from (2,4-dichlorophen)acyl chloride (9.3 g-0.04 mole) and 4-ethyl-thiosemicarbazide (4.77 g-0.04 mole); in 200 ml of methanol). m.p. 197°–198° C.

EXAMPLE 6-5-(2-chlorophenyl)-N-methyl-6H-1,3,4-thiadiazin-2-amine monohydrochloride (2.9 g) (from (2-chlorophen)acyl chloride (4.40 g-0.023 mole) and 4-methyl-thiosemicarbazide (2.42 g-0.023 mole); in 100 ml of methanol). m.p. 173.5°–174.5° C.

EXAMPLE 7-5-(2,4-dichlorophenyl)-N-methyl-6H-1,3,4-thiadiazin-2-amine monohydrochloride (from (2,4-dichlorophen)acyl chloride (11.17 g (0.05 mole) and 4-methyl-thiosemicarbazide (0.05 mole); in 200 ml of methanol, employing an additional recrystallization from methanol/ethyl acetate). m.p. 195° C.

EXAMPLE 8

5-(2,4-Dichlorophenyl)-6H-1,3,4-thiadiazin-2-amine hydrochloride 11.17 g (0.05 mole) of (2,4-dichlorophen)acyl chloride and 4.36 g (0.05 mole) of thiosemicarbazide are stirred and heated in methanol (250 ml) at reflux (65° C.) for 30 minutes. The resultant suspension is allowed to cool and is filtered to yield a first crop of 4.56 g of 5-(2,4-dichlorophenyl)-6H-1,3,4-thiadiazine-2-amine hydrochloride. The reaction mixture is then diluted with ethyl acetate and concentrated in a steam bath giving 6.2 g of the same compound. The products are combined and recrystallized from methanol/ethyl acetate. m.p. 170°–172° C.

EXAMPLE 9

5-(2,4-Dichlorophenyl)-N-2-propenyl-6H-1,3,4-thiadiazin-2-aminemonohydrochloride 3.93 g (0.03 mole) of 4-allyl-thiosemicarbazide and 7.00 g (0.03 mole) of (2,4-dichlorophen)acyl chloride are reacted in accordance with the conditions of EXAMPLE 1. Recrystallization from methanol/methyl acetate produces 8 g of 5-(2,4-dichlorophenyl)-N-2-propenyl-6H-1,3,4-thiadiazin-2-amine. m.p. 188°–189° C.

EXAMPLE 10

5-(2,4-Dichlorophenyl)-N-heptyl-6H-1,3,4-thiadiazin-2-amine monohydrochloride 3.78 g (0.02 mole) of 4-n-heptyl-thiosemicarbazide and 4.67 g (0.02 mole) of (2,4-dichlorophen)acyl chloride are reacted analogously to EXAMPLE 1. After recrystallization from methanol/methyl acetate, 5.2 g of 5-(2,4-dichlorophenyl)-N-heptyl-6H-1,3,4-thiadiazin-2-amine monohydrochloride are produced. m.p. 175°–177° C.

EXAMPLE 11

An illustrative composition for tablets is as follows:

|  | Per Tablet |
| --- | --- |
| (a) 5-(2,4-Dichlorophenyl)-N-methyl-6H-1,3,4-thiadiazin-2-amine monohydrochloride | 100.0 mg |
| (b) Wheat starch | 15.0 mg |
| (c) Lactose | 33.5 mg |
| (d) Magnesium stearate | 1.5 mg |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 12

An illustrative composition for a parenteral injection is the following wherein the quantities are on a weight to volume basis.

|  | Amount |
| --- | --- |
| (a) 5-(2,4-Dichlorophenyl)-N-methyl-6H-1,3,4-thiadiazin-2-amine monohydrochloride | 100.0 mg |
| (b) Sodium chloride | q.s. |
| (c) Water for injection to make | 20 ml |

The composition is prepared by dissolving the active ingredient (a) and sufficient sodium chloride in water for injection to render the solution isotonic. The composition may be dispensed in a single ampoule containing 100 mg of the active ingredient for multiple dosage or in 20 ampoules for single dosage.

EXAMPLE 13

An illustrative composition for hard gelatin capsules is as follows:

|  | Amount |
| --- | --- |
| (a) 5-(2,4-Dichlorophenyl)-N-methyl-6H-1,3,4-thiadiazin-2-amine monohydrochloride | 200.0 mg |
| (b) Talc | 35.0 mg |

The composition is prepared by passing the dry powders of (a) and (b) through a fine mesh screen and mixing them well. The powder is then filled into No. 0 hard gelatin capsules at a net fill of 235 mg per capsule.

EXAMPLE 14

An illustrative composition for pills is the following:

|  | Per Pill |
| --- | --- |
| (a) 5-(2,4-Dichlorophenyl)-N-methyl-6H-1,3,4-thiadiazin-2-amine monohydrochloride | 200 mg |
| (b) Corn starch | 130 mg |
| (c) Liquid glucose | 20 ml |

The pills are prepared by blending the active ingredient (a) and the corn starch; then adding the liquid glucose with thorough kneading to form a plastic mass from which the pills are cut and formed.

EXAMPLE 15

The compounds of each of the preceding examples can be administered as an anti-convulsant for the treatment of, e.g., status epilepticus, severe recurrent convulsive, petit mal, grand mal, or psychomotor seizures, in a patient in which the prevention of such seizures is desired of as an anioxylic agent to ameliorate the anxiety, tension, agitation and irritability associated with psychoneurotic reaction, psychophysiological reaction or personality disorder and to ameliorate the anxiety associated with pathological depression and with alcohol withdrawal in a patient exhibiting such symptoms.

I claim:

1. A compound of the formula

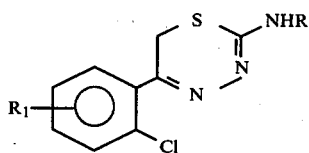

wherein R is H, $C_{1-5 \text{ or } 7}$-straight or branched chain alkyl or allyl and $R_1$ is H or Cl, and the pharmaceutically acceptable acid addition salts thereof.

2. A compound of claim 1, wherein $R_1$ is 4-Cl.

3. A compound of claim 2, wherein R is $C_{1-5}$ straight or branched chain alkyl or allyl.

4. 5-(2,4-dichlorophenyl)-N-methyl-6H-1,3,4-thiadiazin-2-amine monohydrochloride, a compound of claim 1.

5. A pharmaceutical composition comprising in unit dosage form about 5-500 mg of a compound of claim 1 and a significant amount of a pharmaceutically acceptable carrier.

6. A method of achieving an anxiolytic or anticonvulsant effect in a patient which comprises administering to a patient in which such effect is desired an amount of a compound of claim 1 to the patient effective to induce such effect.

7. A method of achieving an anxiolytic effect in a patient which comprises administering to a patient in which such effect is desired an amount of a compound of claim 1 to the patient effective to induce such an effect.

8. A method of claim 6, wherein the compound administered is 5-(2,4-dichlorophenyl)-N-methyl-6H-1,3,4-thiadiazin-2-amine monohydrochloride.

9. A method of claim 6, wherein the compound administered is 5-(2,4-dichlorophenyl)-N-2-propenyl-6H-1,3,4-thiadiazin-2-amine.

* * * * *